United States Patent [19]
Ye et al.

[11] Patent Number: 6,106,858
[45] Date of Patent: *Aug. 22, 2000

[54] MODULATION OF DRUG LOADING IN MULTIVESCULAR LIPOSOMES

[75] Inventors: Qiang Ye, San Diego; Nandini Katre, Solana Beach; Mantripragada Sankaram, San Diego, all of Calif.

[73] Assignee: SkyePharma, Inc., San Diego, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/925,532

[22] Filed: Sep. 8, 1997

[51] Int. Cl.[7] .................................................. A61K 9/127
[52] U.S. Cl. ............................ 424/450; 264/4.1; 264/4.3
[58] Field of Search ...................................... 424/480, 417, 424/1.21, 9.321, 9.51; 436/829; 935/54; 264/4.1, 4.3

[56] References Cited

U.S. PATENT DOCUMENTS

| | | |
|---|---|---|
| Re. 35,192 | 3/1996 | Reese . |
| 5,049,392 | 9/1991 | Weiner ..................................... 424/450 |
| 5,077,056 | 12/1991 | Bally et al. . |
| 5,091,187 | 2/1992 | Hayes . |
| 5,204,112 | 4/1993 | Hope et al. . |
| 5,211,955 | 5/1993 | Legros et al. . |
| 5,227,165 | 7/1993 | Domb et al. . |
| 5,227,170 | 7/1993 | Sullivan .................................. 424/450 |
| 5,244,678 | 9/1993 | Legros et al. . |
| 5,246,707 | 9/1993 | Haynes . |
| 5,261,903 | 11/1993 | Dhaliwal et al. . |
| 5,321,012 | 6/1994 | Mayer et al. ............................ 514/25 |
| 5,334,381 | 8/1994 | Unger . |
| 5,334,391 | 8/1994 | Clark et al. . |
| 5,451,408 | 9/1995 | Mezei et al. . |

OTHER PUBLICATIONS

Shakiba, et al., "Evaluation of Retinal Toxicity and Liposome Encapsulation of the Anti–CMV Drug 2'–nor–cyclic CMP," *Investigative Opthalmology and Visual Science*, No. 10, 34:2903–2910, Sep. 1993.

Frucht–Perry, et al., "Fibrin–Enmeshed Tobramycin Liposomes: Single Application Topical Therapy of . . . ," *Cornea*, No. 5, 11:393–397, Sep. 1992.

Assil, et al., "Tobramycin Liposomes. Single Subconjunctival Therapy of . . . ," *Investigative Opthalmology and Visual Science*, No. 13, 32:3216–3220, Dec. 1991.

Assil, et al., "Liposome Suppression of Proliferatative Vitreoretinopathy. Rabbit . . . ," *Investigative Opthalmology and Visual Science*, No. 11, 32:2891–2897, Oct. 1991.

(List continued on next page.)

*Primary Examiner*—Gollamudi S. Kishore
*Attorney, Agent, or Firm*—Fish & Richardson P.C.

[57] ABSTRACT

Disclosed is a method for making liposomes, for example multivesicular liposomes (MVLs), containing one or more biologically active agents, wherein the loading of the active agents into the liposomes is modulated by adjusting the osmolarity of the aqueous component into which the agents are dissolved prior to encapsulation. To increase the loading of the active agent, the osmolarity of the aqueous component is reduced, and to decrease the loading of the active agent, the osmolarity of the aqueous component is increased. In the making of MVLs, the process involves dissolving the active agent and an optional osmotic excipient in a first aqueous component encapsulated within the liposomes. For any given concentration of drug, the osmolarity of the first aqueous component can be adjusted by increasing or decreasing the concentration or molecular weight of the osmotic excipients used therein. The rate of release of the active agent into the surrounding environment in which the liposomes are introduced can be simultaneously controlled by incorporating into the lipid component used in the formulation at least one long chain amphipathic lipid. For example, the amphipathic lipid can have from about 13 to about 28 carbons in its carbon chain. Use of the long chain amphipathic lipid in the lipid component is particularly helpful in controlling the release rate and encapsulation efficiency for high drug load formulations.

46 Claims, 2 Drawing Sheets

OTHER PUBLICATIONS

Turski, et al., "Magnetic Resonance Imaging of Rabbit Brain After Intracarotid Injection . . . ," *Magnetic Resonance in Medicine*, No. 2, 7:184–196, Jun. 1996.

Skuta et al., "Filtering Surgery in Owl Monkeys Treated With the Antimetabolite . . . ," *American Journal of Opthalmology*, No. 5, 103:714–716, May 15, 1987.

Assil, et al., "Multivascular Liposomes. Sustained Release of the Antimetabolite . . . ," *Archives of Opthalmology*, No. 3, 105:400–403, Mar., 1987.

Barbet, et al., "Weak Acid–Induced Release of Liposome–Encapsulated Carboxyfluorescein," *Biochimica et Biophysica Acta*, No. 3, 772:347–356, May 30, 1984.

Kim, et al., "Preparation of Cell–Size Unilamellar Liposomes with High Captured Volume and Defined Size . . . ," *Biochim. Biophys. Acta*, 646:1–9, 1981.

Kim, et al., "Preparation of Multivesicular Liposomes," *Biochim. Biophys. Acta*, 728: 339–348, 1983.

Kim, et al., "Preparation of Multialmellar Vesicles of Defined Size–Distribution by Solvent–Spherule . . . ," *Biochim. Biophys. Acta*, 812: 793–801, 1985.

Kim, et al., "Multivesicular Liposomes Containing Cytarabine Entrapped in the Presence of . . . ," *Cancer Treat. Rep.*, 71: 705–711, 1987.

Kim, et al., "Multivescular Liposomes Containing Cytosine 1–β–D–Arabinofuranosylcytosine for Slow–Release Intrathecal Therapy," *Cancer Research*, 47: 3935–3937, 1987.

Kim, et al., "Multivesicular Liposomes Containing Cytosine for Slow Release . . . ," *Cancer Treat. Rep.*, 71: 447–450 1987.

Kim, et al., "Modulation of the Peritoneal Clearance of Liposomal Cytosine Arabinoside by . . . ," *Cancer Chemother. Pharmacology*, 19:307–310, 1987.

Roy, et al., "Multivesicular Liposomes Containing Blemomycin for Subcutaneous Administration," *Cancer Chemother. Pharmacology*, 28: 105–108, 1991.

Kim, et al., "Prolongation of Drug Exposure in Cerebrospinal Fluid by Encapsulation Into . . . ," *Camcer Research Pharmacology*, 55: 1596–1598, Apr. 1, 1993.

Kim, et al., "Driect Cerebrospinal Fluid Delivery of an Antiretroviral Agent Using . . . ," *Jrnl. Of Infectious Diseases.*, 162: 750–752, 1990.

Chamberlain, et al., "Treatmentof Leptomeningeal Metastasis with Intraventricular Administration of . . . ," *Archives of Neurol.*, 50: 261–264, 1993.

Chatelut, et al., "A Slow–Release Methotrexate Formulation for Intrathecal Chemotherapy," *Cancer Chemother. Pharmacol.*, 32:179–182, 1993.

Russack, et al., "Quantitative Cerebrospinal–Fluid Cytology in Patients Receiving Intracavitary Chemotherapy," *Ann. Neurol.*, 34:108–112, 1993.

Kim, et al., "Extended Cerebrospinal–Fluid Cytarabine Exposure Folling Intrathecal Administration of DTC 101," *J. Clin. Oncol.*, 11:2186–2193, 1993.

Kim, "Liposomes as Carriers of Cancer Chemotherapy: A Review," *Drugs*, No. 4, 46:618–638, 1993.

Kim, et al., "Extended–Release Formulation of Morphine for Subcutaneous Administration," *Cancer Chemother. Pharmacol.*, 33:187–190, 1993.

Ishii, "Production and Size Control of Large Unilamellar Liposomes by Emulisification," *Liposome Technology*, 1:111–121, 1993.

Cullis, et al., "Structural Properties and Functional Roles of Phospholipids In . . . ," *Phospholipids and Cellular Regulation*, 1:65–123, 1985.

Bonetti, et al., "An Extended–Release Formulation of Methotrexate For Subcutaneous . . . " *Cancer Chemotherapy and Pharmacology*, In Press, 1994.

Grunor, et al., "Novel Multilayered Lipid Vesicles: Comparison of Physical Characteristics of Multilamellar Liposomes and Stable Plurilamellar Vesicles," *Biochemistry*, No. 12, 24:2833–2842, Jun. 4, 1985.

Narhi, etal., "Role of Native Disulfide Bonds in the Structure and Activity of Insulin–like Growth Factor 1: Genetic Models of Protein–Folding Intermediates," Biochemistry, No. 19:5214–5221, 1993.

MODULATION OF DRUG LOADING IN MULTIVESCULAR LIPOSOMES

BACKGROUND OF THE INVENTION

1. Field of the Invention

The present invention relates to a method for controlling loading of active agents into liposomes. More particularly, the present invention relates to methods for modulating loading of active agents into multivesicular liposomes.

2. Description of Related Art

Optimal treatment with many drugs requires that the drug level be maintained at a specified level for a prolonged period of time. For example, optimal anti-cancer treatment with cell cycle-specific antimetabolites requires maintenance of a cytotoxic drug level for a prolonged period of time. Cytarabine is a highly schedule-dependent anti-cancer drug. Because this drug kills cells only when they are synthesizing DNA, prolonged exposure at therapeutic concentration of the drug is required for optimal therapeutic effect. The therapeutic effectiveness of such agents is often further complicated by the fact that the half-life after an intravenous or subcutaneous dose may be as short as a few hours. To achieve optimal therapeutic effect against cancer cells with a cell cycle phase-specific drug like cytarabine, there are two major requirements: first, the cancer cells must be exposed to a high concentration of the drug without doing irreversible significant harm to the host; and second, the tumor must be exposed to the drug for a prolonged period of time to maximize the number of cancer cells that are contacted during DNA synthesis, the susceptible portion of the cycle of cell proliferation. This kind of treatment regimen requires a high drug load in a slow release formulation.

Certain other types of drugs are so toxic that it is important to maintain a low level of the drug over an extended period of time. For instance, amikacin is an aminoglycoside antibiotic with clinically significant activity against strains of both gram negative and gram positive bacteria. Under existing therapeutic procedures, the drug is normally administered by intravenous or intramuscular routes on a once or twice a day schedule. The most commonly used clinical dose is 15 mg/Kg/day, which is equivalent to a maximum recommended daily dose of 1 g per day. However, administration of the drug by spaced injections results in systemic exposure to the patients, and depending on the drug, increases risk of toxic side effects. Consequently, a local depot slow-release preparation for treatment of infections such as those confined to a local region of soft tissue or bone would be advantageous in increasing local tissue levels of the drug, compared with therapeutic systemic doses, while reducing or avoiding the systemic toxicity of the free drug. If the drug is highly toxic or the treatment regimen requires a low therapeutic dose, a relatively low drug load in a slow release formulation is beneficial.

One approach which has been used to provide controlled release compositions for drug delivery is liposome encapsulation. Among the main types of liposomes, multivesicular liposomes (Kim, et al., *Biochim. Biophys.* Acta; 728:339–348, 1983), are uniquely different from unilamellar liposomes (Huang, *Biochemistry;* 8:334–352, 1969; Kim, et al., *Biochim. Biophys.* Acta; 646:1–10, 1981), multilamellar liposomes (Bangham, et al., *J. Mol. Bio.*, 13:238–252, 1965), and stable plurilamellar liposomes (U.S. Pat. No. 4,522,803). In contrast to unilamellar liposomes, multivesicular liposomes contain multiple aqueous chambers. In contrast to multilamellar liposomes, the multiple aqueous chambers of multivesicular liposomes are non-concentric.

The prior art also describes methods for producing multivesicular liposomes (Kim, et al., *Biochim. Biophys.* Acta, 728:339–348, 1983). However, the encapsulation efficiency of some small molecules, such as cytosine arabinoside, also known as cytarabine or Ara-C, proved relatively low, and the release rate of encapsulated molecules in biological fluids was faster than is therapeutically desirable. EP 0 280 503 B1 discloses a method developed for controlling the release rate of encapsulated molecules from multivesicular liposomes wherein a hydrochloride is introduced into the encapsulation process to control the rate of release in biological fluids (of the active agent. Further research, disclosed in WO 95/13796, has shown that the release rate of agents from multivesicular liposomes in human plasma can be controlled by introduction of a non-hydrochloride acid into the aqueous solution in which the agent is dissolved prior to forming the multivesicular liposome U.S. Pat. No. 5,077,056 discloses studies that show the rate of release of the encapsulated biological agent from liposomes into an aqueous environment can be modulated by introducing protonophores or ionophores into liposomes to create a membrane potential. In addition, a method is known (U.S. Pat. No. 5,186,941) for controlling the release rate of drugs from vesicle compositions wherein the liposomes containing a therapeutic agent encapsulated are suspended in a solution containing sufficient solute to provide an osmolarity substantially isotonic with respect to that of the solution within the vesicles, and hypertonic with respect to physiological saline. In multivesicular liposomes, it is also known (WO 96/08253) to control the rate of release of active agents by introducing an osmotic spacer into the aqueous solution in which the active agent is dissolved prior to formation of the multivesicular liposomes.

In addition to the biologically active agent and acids or osmotic spacers intended to control the rate of release of the biologically active agent from the liposomes, it is common practice to coencapsulate compounds that are intended to serve any of a number of helper functions. For instance, certain biologically active compounds retain activity only when kept at a particular pH. Thus acids or buffers are often necessarily encapsulated in addition to the active agent to control the pH of the drug environment. In other cases, a counterion is incorporated to enhance solubility of a biologically active agent that has a low solubility.

These methods for producing liposome formulations with slow release characteristics have sometimes proven incompatible with the goal of producing liposomes containing a high load of active agent with good encapsulation efficiency so that little of the expensive active agent is wasted by failure to capture it within the liposomes.

Thus the need exists for new methods for producing liposomes, for instance multivesicular liposomes (MVLs), that allow for control of drug loading, either high or low, while maintaining desirable slow release of the active agent into storage and biological fluids. Of particular interest is the development of high-load, controlled release formulations for peptides and proteins. A need also exists for new methods of achieving these goals without sacrifice of high encapsulation efficiency to avoid the waste of expensive active agents, such as drug and therapeutic proteins.

SUMMARY OF THE INVENTION

The present invention provides a method for modulating the loading of biologically active agent into liposomal formulations. The concentration of the biologically active agent in the final product is modulated by adjusting the osmolarity of the aqueous component into which the active agent is dissolved for encapsulation. An inverse relation between osmolarity and drug loading has been discovered, with the loading of active agent increasing as the osmolarity of the aqueous component decreases. Thus, liposomes with either high drug loading or low drug loading can be achieved by manipulation of the osmolarity of the drug-containing solution prior to encapsulation. Moreover, it has been discovered that modulation of drug loading, particularly to achieve high drug loading, can be accomplished without sacrifice of either high encapsulation efficiency in the method of manufacture or desirable controlled release of drug from the final product in use.

Liposomes made by the method of this invention achieve greatly improved results by providing a desired amount of the active agent within a given volume of injectable or implatable liposome formulation and provide sustained release of drug at a therapeutically desirable level when introduced to an in vivo site. The general principle followed in order to modulate loading of active agents into liposomal formulations is illustrated herein by reference to manufacture of multivesicular liposomes (MVLs).

Drug loading in liposomes is modulated by controlling the osmolarity of the aqueous solution that is encapsulated during manufacture of the liposomes. Osmolarity is the sum of the molar concentrations of solutes present in the aqueous solution, including the biologically active substance and any helper molecules, such as osmotic excipients used to slow the release rate of the active agent. If the solute is present in a dissociated, ionized, or aggregated form, osmolarity is defined as the sum of the molar concentrations of the dissociated, ionized or aggregated forms. The contribution to the osmolarity of a solution made by any solute in the solution is approximately equivalent to the concentration of the solute in the solution divided by its molecular weight. Thus, as a general principle, the larger the molecular weight of a solute, the smaller the osmolarity of the solute, and the smaller the contribution of that solute to the overall osmolarity of the solution.

It is well known that the level of drug loading in liposomes is directly proportional to the concentration of the biologically active agent. Accordingly, a high level of the active agent must be dissolved in an aqueous solution to be encapsulated in order to obtain liposomes with a high level of drug loading. However, loading cannot always be increased by adding a further concentration of the active agent. Solutes other than the biologically active agent present in the aqueous solution used during manufacture of liposomes tend to reduce the amount of the biologically active agent that can be loaded into the liposomes. Therefore, if the solution also contains osmotic excipients necessary to regulate the solubility or bioactivity of the active agent, the beneficial effects of the helper osmotic excipients in the solution must be balanced against their adverse effect upon drug loading.

To enhance drug loading, the osmolarity of the aqueous solution can be decreased, without decreasing the concentration of the active agent dissolved therein, either by reducing the concentration of the osmotic excipients, or by replacing a low molecular weight osmotic excipient by a higher molecular weight osmotic excipient of comparable function, or both. For instance, if the osmotic excipient is a buffer used to obtain the solubility of a particular concentration of biologically active agent, a high molecular weight buffer is selected to obtain high loading of the active agent Conversely, to decrease the loading in such a situation, a lower molecular weight buffer would be employed.

Although these principles are operative in the making of all types of liposomes, they are illustrated herein in MVL formulations containing such various active agents as cytarabine, leuprolide, enkephalin, morphine, and insulin-like growth factor I (IGF-I). In these studies it was found that, for any selected concentration of biologically active agent, drug loading during manufacture can be effectively modulated in MVLs by varying the contributions made by the osmotic excipients in the solution to the overall osmolarity of a first aqueous component. This principle is illustrated in the examples herein by adjusting the concentration of a model osmotic excipient commonly used in liposomal formulations, either sucrose or glycylglycine. By this method, MVL formulations can be produced having a broad range of loading levels for any given biologically active agent.

In the method of manufacture of multivesicular liposomes (MVLs) having controlled drug loading, a lipid component containing at least one amphipathic lipid and one neutral lipid dissolved in one or more organic solvents is mixed with an immiscible first aqueous component containing one or more biologically active agents to be encapsulated and, optionally, one or more osmotic excipients, such as a helper molecule. The loading of the active agent in the final formulation will depend upon the overall osmolarity of this first aqueous component, which is the sum of the osmolarity contributed by each of the solutes dissolved in the first aqueous component, including the active agent and any osmotic excipients.

Once the osmolarity of the first aqueous component has been adjusted to achieve the desired loading of the active agent in the final product, a water-in-oil emulsion is formed by mixing of the two immiscible components. The water-in-oil emulsion is then mixed into a second immiscible aqueous component to form solvent spherules. The organic solvent is finally removed from the solvent spherules, for example by evaporation, to cause them to aggregate into MVLs. In the final step of the process, the MVLs are suspended in an aqueous medium, such as normal saline. A composition containing a therapeutically effective dose of active agent on a weight by volume of formulation basis can be obtained by increasing or decreasing the volume of the medium in which the MVLs containing the active agent are suspended.

To maintain a high encapsulation efficiency (or percent yield) during formulation of the MVLs and ensure that release of the active agent in use is at a slow therapeutically effective rate, the lipid component contains one or more amphipathic lipid having from about 13 to about 28, for example, about 18 to 22, carbons in its carbon chain.

DESCRIPTION OF PREFERRED EMBODIMENTS

Figure 1:
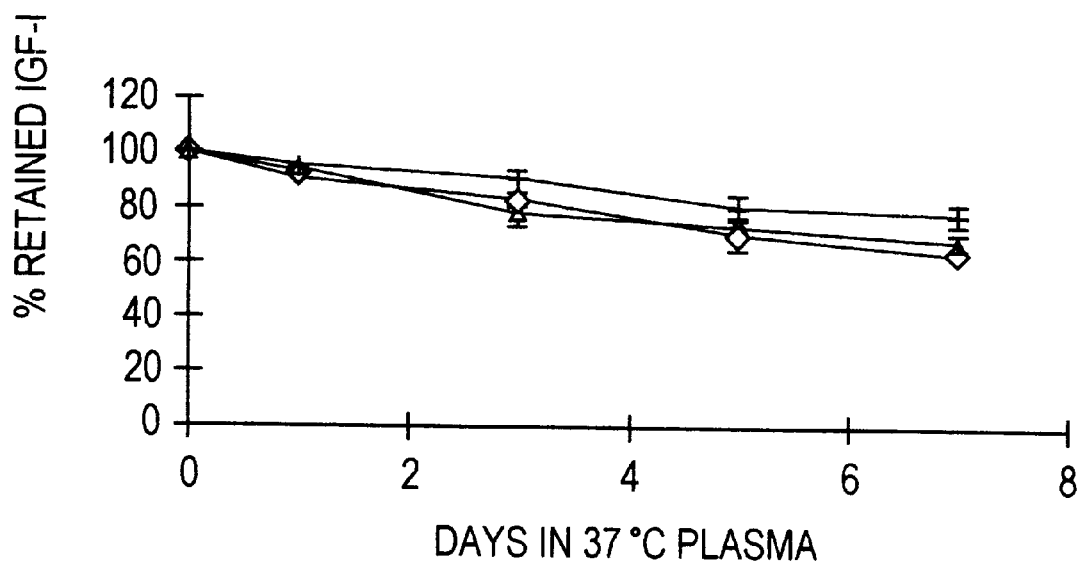
FIG. 1 is a graph showing the percent of IGF-I retained in MVLs during in vitro incubation (rate of release) over 7 days in plasma at 37° C. During manufacture the concentrate thereof sucrose or glycylglycine as an osmotic excipient was varied in the aqueous component to control drug loading. $\Diamond$=80 mg/mL IGF-I and 2.5 w/v % sucrose (113.5 mOsm); $\nabla$=80 mg/mL IGF-I and 1 w/v % glycylglycine (113.5 mOsm); +=50 mg/mL IGF-I and 1 w/v % sucrose (63.5 mOsm). Error bars represent standard deviation.

In this invention, a method is provided whereby the amount of biologically active agent encapsulated per unit volume of liposome formulation is modulated by adjusting the osmolarity of the encapsulated aqueous component containing the drug. In this method, a reduction in osmolarity of the aqueous component into which the active agent is dissolved prior to encapsulating yields an increased concentration of the active agent in the final MVL suspension on a weight by volume basis, and visa versa.

There are at least three types of liposomes. The term "multivesicular liposomes (MVL)" as used throughout the specification and claims means man-made, microscopic lipid vesicles comprising lipid membranes enclosing multiple non-concentric aqueous chambers. In contrast, "multilamellar liposomes or vesicles (MLV)" have multiple "onion-skin" concentric membranes, in between which are shell-like concentric aqueous compartments. Multilamellar liposomes and multivesicular liposomes characteristically have length-weighted mean diameters in the micrometer range, usually from 0.5 to 25 $\mu$m. The term "unilamellar liposomes vesicles (ULV)" as used herein refers to liposomal structures having a single aqueous chamber, usually with a mean diameter range from about 20 to 500 nm.

Multilamellar and unilamellar liposomes can be made by several relatively simple methods. The prior art describes a number of techniques for producing ULV and MLV (for example U.S. Pat. Nos. 4,522,803 to Lenk; 4,310,506 to Baldeschweiler; 4,235,871 to Papahadjopoulos; 4,224,179 to Schneider, 4,078,052 to Papahadjopoulos; 4,394,372 to Taylor 4,308,166 to Marchetti; 4,485,054 to Mezei; and 4,508,703 to Redziniak).

By contrast, production of multivesicular liposomes requires several process steps. Briefly, the preferred method for making MVL is as follows: In the first step a "water-in-oil" emulsion is made by dissolving at least one amphipathic lipid and at least one neutral lipid in one or more volatile organic solvents for the lipid component. To the lipid component is added an immiscible first aqueous component containing a biologically active agent to be encapsulated and one or more helper molecules i.e., osmotic excipients, that provide useful and beneficial properties to the MVLs. The mixture is emulsified, and then mixed with a second immiscible aqueous component to form a second emulsion. The second emulsion is mixed either mechanically, by ultrasonic energy, nozzle atomization, and the like, or by combinations thereof, to form solvent spherules suspended in the second aqueous component. The solvent spherules contain multiple aqueous droplets with the biologically active agent to be encapsulated dissolved in them (see Kim et al., *Biochem. Biophys.* Acta, 728:339–348, 1983). For a comprehensive review of various methods of ULV and MLV preparation, refer to Szoka, et al. *Ann. Rev. Biophys.* Bioeng. 9:465–508, 1980.

The term "solvent spherule" as used throughout the specification and claims means a microscopic spheroid droplet of organic solvent, within which are multiple smaller droplets of aqueous solution. The solvent spherules are suspended and totally immersed in a second aqueous solution.

The term "neutral lipid" means an oil or fat that has no membrane-forming capability by itself and lacks a hydrophilic "head" group.

The term "amphipathic lipid" means a molecule that has a hydrophilic "head" group and hydrophobic "tail" group and has membrane-forming capability.

The term "zwitterionic lipid" means an amphipathic lipid with a net charge of zero at pH 7.4.

The term "anionic lipid" means an amphipathic lipid with a net negative charge at pH 7.4.

The term "cationic lipid" means an amphipathic lipid with a net positive charge at pH 7.4.

For making multivesicular liposomes, it is required that at least one amphipathic lipid and one neutral lipid be included in the lipid component. The amphipathic lipids can be zwitterionic, anionic, or cationic lipids. Examples of zwitterionic amphipathic lipids are phosphatidylcholines, phosphatidylethanolamines, sphingomyelins etc. Examples of anionic amphipathic lipids are phosphatidylglycerols, phosphatidylserines, phosphatidylinositols, phosphatidic acids, etc. Examples of cationic amphipathic lipids are diacyl trimethylammoniumpropane and ethyl phosphatidylcholine. Examples of neutral lipids include diglycerides, such as diolein, dipalmitolein, and mixed caprylincaprin diglycerides; triglycerides, such as triolein, tripalmitolein, trilinolein, tricaprylin, and trilaurin; vegetable oils, such as soybean oil; squalene; tocopherol; and combinations thereof. Additionally, cholesterol or plant sterols can be used in making multivesicular liposomes.

As used herein, the term "biologically active agent" or "active agent" when used to describe agents present in the chambers of the multivesicular liposome or in the aqueous solution used during manufacture of liposomes, includes agents which possess biological activity targeted in treatment of a particular disease state, either in the form released from vesicle, or in a form that becomes active after release from the vesicle chamber. For example biologically active agents include drugs and pro-drugs that are converted upon interaction with an enzyme into an active moiety with therapeutic activity. Insecticides, pesticides, and agents with desired cosmetic application are also encompassed by the term "biologically active agent."

The term "osmotic excipient" means any biologically compatible solute molecule in an aqueous solution that is not the biologically active agent. Both electrolytes and non-electrolytes function as osmotic excipients. In determining whether any particular molecule will function as an osmotic excipient or in determining the concentration of osmotic excipient in a solution, for example one encapsulated within a multivesicular liposome, consideration must be given to whether, under conditions within the solution (for example, pH), the molecule is wholly or partially ionized. It should also be determined whether such ions will permeate the lipid membrane (Mahendra K. Jain, van Nostrand Reinhold Co., *The Bimolecular Lipid Bilayer Membrane*, 1972, 470 pp.). One skilled in the art will appreciate that for use in the present invention, the osmotic excipient must be selected so as to avoid those that would prove toxic or otherwise harmful to a subject undergoing therapy by use of the liposome. Those of skill in the art can readily evaluate the suitability of a given osmotic excipient for use in the present invention without resort to undue experimentation.

Certain osmotic excipients have inherent biological activity, and many facilitate the biological activity of the biologically active agent. For instance, calcium ions may be coencapsulated as a counterion to increase shelf life or facilitate bioavailability of a drug, but are not sufficient to accomplishing the therapeutic or other utility of the MVL formulation. In addition, various stabilizers may be present. Certain agents commonly classified as excipients may actually possess direct biological activity from very slight to quite significant. For example, the common excipient mannitol can also act biologically as a diuretic, Even water may act biologically to cure dehydration, but when these compounds are used as osmotic excipients rather than active agents, they are relatively interchangeable with others that perform the same helper function. Osmotic excipients, that may be used to form multivesicular liposomes and to modulate the drug loading of the encapsulated agent from multivesicular liposomes include, but are not limited to, glucose, sucrose, trehalose, succinate, glycylglycine, gluconic acid, cyclodextrin, arginine, galactose, mannose, maltose, mannitol, glycine, lysine, citrate, sorbitol, dextran, and suitable combinations thereof. Table 1 below compares the osmolarity of sucrose and glycylglycine solutions at different concentrations.

TABLE 1

| Sucrose or Glycylglycine (w/v %) | Osmolarity for sucrose (mOsm) | Osmolarity for Glycylglycine (mOsm) |
| --- | --- | --- |
| 0.5 | 15 | 38 |
| 1.0 | 30 | 76 |
| 1.5 | 45 | 114 |
| 2.0 | 60 | 152 |
| 2.5 | 76 | 189 |
| 3.0 | 91 | 227 |
| 4.0 | 123 | 303 |
| 5.0 | 156 | 379 |
| 6.0 | 190 | 455 |
| 7.0 | 225 | 530 |
| 8.0 | 261 | 606 |

[1]Sucrose data are from *Handbook of Physics and Chemistry*, 67th Edition

[2]Glycylglycine data are calculated based on the molar concentration

Those of ordinary skill in the art can readily ascertain and envision various combinations of excipients that can be utilized in the vesicles of the invention without resorting to undue experimentation.

As used herein the term "therapeutically effective amount or level" means the amount of a biologically active agent necessary to induce a desired pharmacological effect. The amount can vary greatly according to the effectiveness of a particular active agent, the age, weight, and response of the individual host as well as the nature and severity of the host's symptoms. Accordingly, there is no upper or lower critical limitation upon the amount of the active agent. The therapeutically effective amount to be employed in the present invention can readily be determined by those skilled in the art.

As used herein, "drug loading" means, in a general quantitative sense, the amount of the biologically active agent loaded into the product liposome suspension. It is a measure, therefore, of the amount of active agent available in a unit volume of liposome formulation to be delivered to the patient during use. More particularly, "drug loading" means the ratio of encapsulated drug per unit volume of liposome suspension to the percent encapsulated volume in the liposomes themselves. It is approximately equal to the concentration of the active agent in the suspension divided by the lipocrit of the suspension for low percent free drug.

$$\text{Drug Loading} = \left[\frac{\text{(Drug Encapsulated Per Unit Volume of Liposome Suspension)}}{\text{(Percent encapsulated volume in Liposomes)}}\right]$$

$$\approx \text{(Drug Concentration of Liposome Suspension)}/\text{Lipocrit}$$

As used herein, "percent encapsulation of drug, or other compound" means the ratio of the amount of compound to be encapsulated in the final suspension of the liposome manufacturing process to the total amount of compound to be encapsulated used in the first aqueous solution of the process multiplied by 100.

$$\text{Percent encapsulation of compound} = \left(\left[\frac{\text{Amt. of compound encapsulated}}{\text{Amt. of compound introduced prior to encapsulation}}\right]\right) \times 100$$

As used herein, "lipocrit," which is defined in analogy to hematocrit, means the ratio of the volume occupied by the liposomes to the total suspension volume multiplied by 100.

$$\text{Lipocrit (in percent)} = \left(\left[\frac{\text{Volume occupied by the liposomes}}{\text{Total volume of liposome suspension}}\right]\right) \times 100$$

As used herein, "percent free drug" means the ratio of the amount of drug exterior to the liposomes in the final liposome suspension to the total amount of drug in the final suspension (the final product) multiplied by 100.

$$\text{Percent free drug} = \left(\left[\frac{\text{Amt. of drug exterior to the liposomes in the final product}}{\text{Amt. of drug in final product}}\right]\right) \times 100$$

$$\approx (1 - \text{Lipocrit}) \times \left(\frac{\text{Drug concentration exterior to the liposomes}}{\text{Drug concentration of liposome suspension}}\right)$$

The methods for determining these parameters are illustrated in Example 7 of this application.

Wherever possible, the use of osmotic excipients is reduced to a minimum or avoided to attain high loading of the biologically active agent. In this case, drug loading is directly dependent upon the concentration of the active agent in the solution to be encapsulated, as the osmolarity is largely attributable to the active agent. When it is not possible to use a first aqueous solution that is free of osmotic excipients, the osmolarity of the first aqueous component can be decreased by substituting high molecular weight osmotic excipients for low molecular weight excipients, such as high molecular weight buffer or stabilizer for one having a lower molecular weight. Also, in choosing a negative counterion for a drug, a counterion of high molecular weight can be substituted for one having a lower mechanical weight. For example, in morphine hydrochloride, the chloride ion can be replaced by sulfate or a negative ion with even greater molecular weight such as phosphate.

Conversely, when it is desirable to produce a low load formulation of the biologically active agent, as when the biologically active agent is toxic at high concentrations, the osmolarity of the first aqueous solution can be increased by choosing low molecular weight osmotic excipients to increase its osmolarity.

The lower limit for osmolarity of the first aqueous component can be close to zero, as in the case where the biologically active agent is a high molecular weight protein or other macromolecule and no osmotic excipients are used. On the other hand, the osmolarity of the first aqueous component can sometimes be as high as about 1000 mOsm or higher without detrimental or toxic effect in use because many of the excipients can pass out of the liposome during the process of manufacturing. Generally, however the osmolarity of the first aqueous component is in the range from about 0.01 mOsm to about 1100 mOsm, for example in the range from about 5 mOsm to about 400 mOsm.

The osmolarity of the encapsulated aqueous component in the final liposomal product is generally isotonic with respect to the aqueous environment in which the MVLs are stored (such as 0.9 wt % NaCl, or normal saline) or into which the MVLs are introduced for use, such as serum or other physiologically relevant aqueous environment. However, the osmolarity of the aqueous component in the final MVL product can also be hypertonic to provide an optimum decrease in the rate of release of the biologically active agent from the liposomes. Therefore, it is contemplated within the scope of this invention that the aqueous component in the MVL product can be hypotonic, isotonic or hypertonic with respect to the storage medium or the aqueous environment into which the biologically active agent is to be released.

The osmolarity of normal saline is similar to that of human plasma and other in vivo environments, such as cerebrospinal fluid, synovial fluid, and subcutaneous and intramuscular spaces. Therefore, saline can be used as a predictive model of MVL drug release in such environments. Because the preferred use of the MVLs of the invention is for in vivo injection or implantation into tissue or body cavities (for instance, as drug depots), they are usually stored in a medium such as normal saline, phosphate-buffered saline, or other osmotically similar medium.

The rate of release of active agents from MVLs is generally increased by lowering the osmolarity of the first aqueous component used during manufacturer. However, lowering the osmolarity of the first aqueous component can have a negative effect upon sustained release and encapsulation efficiency). This negative effect can be overcome by using in the lipid component one or more amphipathic lipids having from about 13 to about 28 carbons, for example from about 18 to 22 carbons. This general rule holds whether the carbon chain of the amphipathic lipid is saturated, or whether it contains one or more double bonds. Generally, however, in selecting the lipids to be used in formulating a multivesicular liposome it should be kept in mind that it is possible to use an organic solvent with a lower boiling point when utilizing a lipid with a given number of carbons in the carbon chain, if the lipid contains at least one double bond in the carbon chain. The preferred amphipathic lipids for use in making the multivesicular liposomes of this invention are naturally occurring lipids. The beneficial effects upon encapsulation efficiency and sustained release of the biologically active agent to be obtained by utilizing such long chain amphipathic lipids during manufacture of MVLs is disclosed in copending U.S. patent application Ser. No. 08/723,583, filed Oct. 1, 1996, entitled "Method for Producing Liposomes With Increased Percent of Compound Encapsulated," which is incorporated herein in its entirety.

A representative list of long chain amphipathic lipids useful in the practice of this invention follows. This list is illustrative and not intended to in any way limit the scope of the invention. Also included are the abbreviations used to refer to the phospholipids in this application and in the scientific literature.

DOPC or DC18:1PC=1,2-dioleoyl-sn-glycero-3-phosphocholine

DLPC or DC12:0PC=1,2-dilauroyl-sn-glycero-3-phosphocholine

DMPC or DC14:0PC=1,2-dimyristoyl-sn-glycero-3-phosphocholine

DPPC or DC16:0PC=1,2-dipalmitoyl-sn-glycero-3-phosphocholine

DSPC or DC18:0PC=1,2-distearoyl-sn-glycero-3-phosphocholine

DAPC or DC20:0PC 1,2-diarachidoyl-sn-glycero-3-phosphocholine

DBPC or DC22:0PC=1,2-dibehenoyl-sn-glycero-3-phosphocholine

DC16:1PC=1,2-dipalmitoleoyl-sn-glycero-3-phosphocholine

DC20:1PC=1,2-dieicosenoyl-sn-glycero-3-phosphocholine

DC22:1PC=1,2-dierucoyl-sn-glycero-3-phosphocholine

DPPG=1,2-dipalmitoyl-sn-glycero-3-phosphoglycerol

DOPG=1,2-dioleoyl-sn-glycero-3-phosphoglycerol

Many different types of volatile hydrophobic solvents such as ethers, hydrocarbons, halogenated hydrocarbons, supercritical fluids including but not limited to $CO_2$, $NH_3$, and freons may be used as the lipid-phase solvent. For example, diethyl ether, isopropyl and other ethers, dichloromethane, chloroform, tetrahydrofuran, halogenated ethers, esters and combinations thereof are satisfactory.

Therapeutic biologically active compounds, or drugs, for encapsulation in the methods and compositions of this invention may be selected from the general group consisting of anti-neoplastic agents, anti-infective agents, hormones, anti-depressives, anti-inflammatory agents antiviral agents, anti-nociceptive agents, anxiolytics and biologics.

Representative examples of anti-neoplastic agents useful in the compositions and methods of the present invention include methotrexate, taxol, tumor necrosis factor, chlorambucil, interleukins, etoposide, cytarabine, fluorouracil and vinblastine.

Representative examples of anti-infective agents useful in the compositions and methods of the present invention include amikacin, pentamidine, metronidazole, penicillin, cephalexin, tetracyclin, and chloramphenicol.

Representative examples of anti-viral agents useful in the composition and methods of the present invention include dideoxycytidine, zidovudine, acyclovir, interferons, dideoxyinosine, and ganciclovir.

Representative examples of anxiolytics and sedatives useful in the compositions and methods of the invention include benzodiazepines such as diazepam, barbiturates such as phenobarbital, and other compounds such as buspirone and haloperidol.

Representative examples of hormones useful in the compositions and methods of the present invention include estradiol, prednisone, insulin, growth hormone, erythropoietin, and prostaglandins.

Representative examples of anti-depressives useful in the compositions and methods of the present invention include fluoxetine, trazodone, imipramine, and doxepin.

Representative examples of anti-nociceptives useful in the compositions and methods of the present invention include bupivacaine, hydromorphine, oxycodone, fentanyl, morphine, and meperidine.

The term "biologics" encompasses nucleic acids (DNA and RNA), glucosaminoglycans proteins and peptides, and includes compounds such as cytokines, hormones (pituitary, adrenal, and hypophyseal hormones), growth factors, vaccines etc. Of particular interest are interleukin-2, insulin-like growth factor-1 (IGF-I), interferons, insulin, heparin, leuprolide, granulocyte colony stimulating factor (G-CSF), granulocyte-macrophage colony stimulating factor (GM-CSF), tumor necrosis factor, inhibin, tumor growth factor alpha and beta, Mullerian inhibitory substance, calcitonin, hepatitis B vaccine, DNA or RNA vaccines, DNA for gene transfer, and antisense oligonucleotides.

The biologically active agent can be employed in the present invention in various forms, such as molecular complexes or biologically acceptable salts. Representative examples of such salts are succinate, hydrochloride, hydrobromide, sulfate, phosphate, nitrate, citrate, glucuronate, borate, acetate, maleate, tartrate, salicylate, metal salts (e.g., alkali or alkaline earth), ammonium or amine salts (e.g., quarternary ammonium) and the like. Furthermore, derivatives of the active agents such as esters, amides, and ethers thereof that have desirable retention and release characteristics, but which are readily hydrolyzed by physiological pH or enzymes in vivo, can also be employed as the biologically active agent.

The concentration of the encapsulated biologically active agent can vary from about a few picomoles to about several hundred millimoles. The desirable concentration of biologically active agent will vary depending upon such characteristics as the disease to be treated, the age and condition of the patient, and the particular properties of the agent. In the case where the agent is normally associated with side effects such as toxicity, it is generally desirable to produce an MVL with a lower concentration of agent and utilize a higher concentration of osmotic excipient. The interrelationship of these various parameters can be easily evaluated by one of skill in the art in selecting and producing a given MVL composition without resort to undue experimentation.

High loading formulations obtained by the method of this invention are particularly useful in the pharmaceutical industry for reducing the amount of liposome formulation that must be administered to a subject (i.e. intramuscularly or subcutaneously) to achieve a desired therapeutic concentration of drug in the blood stream. However, the upper useful limit on the amount of drug encapsulated into a given volume of liposome suspension may be dictated by the lipocrit of the suspension. As one skilled in the art will appreciate, it can be difficult to inject a suspension containing liposomes if the lipocrit of the suspension is too high.

The dosage range appropriate for in vivo use in humans of the biologically active agent in multivesicular liposomes of this invention includes the range of 0.001–6,000 mg/M$^2$ of body surface area. While doses outside the foregoing dose range may be given, this range encompasses the breadth of use for practically all the biologically active agents. However, for a particular therapeutic agent, the preferred concentration can be easily ascertained as previously described.

The MVL formulations can be further diluted to obtain an injectable slow release depot formulation of any therapeutically effective total dosage by addition of suspending medium or any physiologically acceptable carrier. Common suitable carriers include aqueous or non-aqueous solutions, suspensions, and emulsions. Examples of non-aqueous solutions are propylene glycol, polyethylene glycol, vegetable oils, such as olive oil, and injectable organic esters such as ethyl oleate. Aqueous carriers include water, alcoholic-aqueous solutions, emulsions or suspensions, including saline and buffered media. Parenteral vehicles include sodium chloride solution, Ringer's dextrose, dextrose, and lactated Ringer's solution. Intravenous vehicles include fluid and nutrient replenishers, electrolyte replenishers (such as those based on Ringer's dextrose), and the like. Preservatives and other additives may also be present, such as, antimicrobials, anti-oxidants, chelating agents, and inert gases (see, *Remington's Pharmaceutical Sciences*, 16th Ed., A. Oslo, ed., Mack, Easton, Pa. 1980).

The multivesicular liposomes may be administered by any desired route; for example, intratumoral, intra-articular (into joints), intra-ocular, intramuscular, intrathecal, intraperitoneal, subcutaneous, intravenous, intralymphatic, oral and submucosal. The multivesicular liposomes may be modified using methods well known in the art by attaching thereto, either directly, or indirectly, such as by means of an excipient molecule or peptide, target-specific ligands, such as antibodies and other receptor specific protein ligands, in order to impart organ or cell target specificity (Malone, et al., *Proc. Nat'l. Acad. Sci*, U.S.A., 86:6077, 1989; Gregoriadis, *Immunology Today*, 11(3):89, 1990; both incorporated by reference).

A series of experiments were conducted to show that the effect of osmolarity upon drug loading is inverse and is independent of other parameters used during the manufacturing process, except for the amount of active agent, which is directly proportional to the amount of active agent that can be loaded in a liposomal formulation. These two parameters therefore must be balanced to obtain any desired level of loading. For example, in Example 1 it was shown that cytarabine can be encapsulated into MVLs using a vortexer mixer and a first aqueous component containing 40 mg/mL of cytarabine in 20 mM citric acid and amounts of sucrose in the range from zero to 8.0 weight/volume percent (w/v %). The corresponding estimated osmolarity of the first aqueous composition in this range of formulations was 185.9 to 446.9 mOsm. The corresponding range of drug loading (Table 2) was from 61.7 to 21.0 mg/ml with % yield of the encapsulation process remaining relatively constant.

By varying the concentration of the active agent and the concentration of the osmotic excipient, the invention yields MVL formulations with a wide range of drug loading for any given active agent. For instance, in Example 2, met-enkephalin was encapsulated into MVLs using a first aqueous component containing 40 or 5 mg/mL of met-enkephalin in 20 mM citric acid, and 0, 2.5, or 5 w/v % sucrose, producing an osmolarity range in the first aqueous component from 35.5 to 191.5 mOsm. The results of these studies (Tables 2 and 3) show that decreasing of osmolarity in the first aqueous component resulted in a proportional increase in drug loading, whether the amount of the active agent in the first aqueous solution was 40 mg/mL or 5 mg/mL. In addition, MVL formulations containing as little as 6.4 mg/mL or as much as 61.7 mg/mL of drug were obtained using the method of the invention. These results illustrate the broad applicability of the principle that underlies the claimed invention.

Further studies were conducted using in the first aqueous component concentrations of IGF-I ranging from 10 to 80 mg/mL, either with or without 100 mM HCl or 25 mM citric acid at constant pH. It was found that solubility and bioavailability of encapsulated IGF-I varied according to pH of the first aqueous component. Studies have shown that up to about 300 mg/mL of IGF-I is soluble at a pH below 5. For all concentrations of IGF-I tested, in the pH range where the drug is soluble, drug loading varied according to the osmolarity. For concentrations of IGF-I in the range from 40 to 300 mg/mL, the solubility was greatest in the range from 2 to 4.8; while the useful solubility range for concentrations of IGF-I in the range from about 1 mg/mL to about 33 mg/mL was from about 1 to about 5.

Additionally, the IGF-I formulations made compare the effects upon drug loading of substituting a non-sugar (glycylglycine) for a sugar (sucrose) as the osmotic excipient. In a number of the formulations, the long-chain amphipathic lipid used to impart slow release properties to the formulations was also switched from DEPC to DOPC without significant change of the trend of modulation of drug loading by adjusting the osmolarity of the first aqueous component. To illustrate that the method of this invention is independent of variables such as the batch size and the method of mixing used during the process of making, the MVL formulations were made in different batch sizes and with different types of mixers. Comparison of the results of these tests in Tables 6A through 6F showed that the inverse relationship between osmolarity and drug loading is not dependent upon the chemical character of any of the osmotic excipients in the first aqueous component, and that, for constant drug concentration, the trend of increased drug loading with decreased osmolarity is consistent, although different batch sizes and methods of mixing can give somewhat different levels of loading.

The following examples illustrate the manner in which the invention can be practiced. It is understood, however, that the examples are for the purpose of illustration, and the invention is not to be regarded as limited to any of the specific materials or conditions therein.

EXAMPLE 1

Preparation of Liposome Formulations

In all of the methods of making MVLs illustrated herein, in the first step, a 'water-in-oil' emulsion was prepared by mixing a lipid component with a first aqueous component. The lipid component contained 0.5–4 mL of 13.20 mM DOPC or DEPC, 19.88 mM cholesterol, 2.79 mM DPPG, and 2.44 mM triolein (Avant Polar Lipids Inc., Alabaster, Ala.) in chloroform (Spectrum Chemical Manufacturing Corp., Gardena, Calif.) as solvent. An equal volume (0.5–4 mL) of a first aqueous solution containing cytarabine, leuprolide, morphine, enkephalin, or IGF-I and varying concentrations of an osmotic excipient was mixed with the lipid component using a variety of mixers to determine the effect of osmolarity upon drug loading and percent yield of the various combinations tested.

Preparation of Cytarabine-containing MVL

For cytarabine, the lipid component contained DEPC, rather than DOPC, and four different first aqueous solutions were prepared, each containing 40 mg/mL of cytarabine (Upjohn Co., Kalamazoo, Mich.) in 20 mM citric acid (Sigma Chemical) and 0, 2, 5 or 8 w/v % of sucrose as the excipient osmotic agent. An emulsion of the lipid and first aqueous components was formed by mixing 0.5 mL of the first aqueous component with 0.5 mL of the lipid component using a Baxter vortexer at the maximum speed (setting 10) for 6 min. To the resulting first emulsion, 2.5 mL of a solution containing 4 wt % glucose and 40 mM lysine (Spectrum Chemicals) was added, respectively. The resulting mixture was emulsified to form a second emulsion with the Baxter vortexer at the maximum speed (setting 10) for 4 sec. The resulting second emulsion, a 'water-in-oil-in-water' double emulsion, was transferred for gentle swirling to a 250 mL Erlenmeyer flask containing 10 mL of a solution of 4 percent by weight glucose and 40 mM lysine. To evaporate the organic solvent (chloroform) from the particles, nitrogen gas was passed over the second emulsion at 37° C. for 20 minutes with gentle shaking. The resulting multivesicular liposomes were washed twice with 50 mL of normal saline by centrifugation at 600×g on a bench top centrifuge, and then resuspended in 0.5–4 mL of normal saline. The estimated osmolarity (mOsm), percent yield, and drug loading of these formulations are shown in Table 2 below.

TABLE 2

| First Aqueous Solution | | | Final Liposome Suspension | | |
|---|---|---|---|---|---|
| Cytarabine (mg/mL) | Sucrose (w/v %) | Other | Estimated Osmolarity (mOsm) | % Yield | Drug Loading (mg/mL) |
| 40 | 8.0 | 20 mM Citric Acid | 446.9 | 57.1 | 21.0 |
| 40 | 5.0 | 20 mM Citric Acid | 341.9 | 62.6 | 30.8 |
| 40 | 2.0 | 20 mM Citric Acid | 245.9 | 77.3 | 45.2 |
| 40 | 0.0 | 20 mM Citric Acid | 185.9 | 69.6 | 61.7 |

These results show that drug loading can be modulated by varying the osmolarity of the first aqueous solution, with decreasing osmolarity resulting in increased drug loading. The increase in drug loading achieved by decreasing osmolarity does not result in a significant variation in the percent yield in the MVL formulation.

EXAMPLE 2

Preparation of Met-Enkephalin-containing Multivesicular Liposome Formulations A lipid component containing DEPC, rather than DOPC, was prepared as in Example 1. The first aqueous component contained 5 mg/mL of met-enkephalin (a pentapeptide) (Sigma Chemical Co., St. Louis, Mo.) in 25 mM citric acid, and 0, 2.5 or 5.0 w/v % of sucrose as osmotic excipient. The remainder of the steps described in Example 1 were carried out to obtain MVLs containing met-enkephalin suspended in normal saline. The estimated osmolarity (mOsm), percent yield, and drug loading of these formulations are shown in Table 3 below:

TABLE 3

| First Aqueous Solution | | | Final Liposome Suspension | | |
|---|---|---|---|---|---|
| Enkephalin (mg/mL) | Sucrose (w/v %) | Other | Estimated Osmolarity (mOsm) | % Yield | Drug Loading (mg/mL) |
| 5 | 5.0 | 25 mM Citric Acid | 191.5 | 77.5 | 6.4 |
| 5 | 2.5 | 25 mM Citric Acid | 111.5 | 71.8 | 13.4 |
| 5 | 0.0 | 25 mM Citric Acid | 35.5 | 72.5 | 50.8 |

The data in Table 3 again show that loading of met-enkephalin is modulated by varying the osmolarity of the first aqueous solution, with decreasing of osmolarity resulting in increased drug loading. Thus the effect is independent of the drug loaded. The percent yield is not significantly changed by a decrease in osmolarity. The effect upon drug loading obtained by varying the osmolarity of the first aqueous component is also found when DEPC is replaced with DOPC in the lipid component during manufacture.

EXAMPLE 3

Preparation of Leuprolide-containing Multivesicular Liposome Formulations

A lipid component containing DOPC, rather than DEPC, was prepared as in Example 1, except that it contained leuprolide and a 3-fold higher molar concentration of all four lipids in the lipid component. The first aqueous component contained 15 mg/mL of leuprolide acetate (Bachem Bioscience Inc., King of Prussia, Pa.) in 100 mM phosphoric acid, and 4.0 or 6.0 w/v % of sucrose as osmotic excipient. The procedures of Example 1 were followed for obtaining the MVLs containing leuprolide, except that 4 mL of the first aqueous component was mixed with 4 mL of the lipid component using a TK Autohomogenizer K at a speed of 9,000 rpm for 8 min to obtain the first emulsion. To the first emulsion, 16 mL of a solution containing 4 wt % glucose and 40 mM lysine (Spectrum Chemicals) was added, respectively. The resulting mixture was emulsified to form a second emulsion with the TK Autohomogeneizer K at a speed of 4,000 rpm for 1 min. The estimated osmolarity (mOsm), percent yield, and drug loading of these formulations are shown in Table 4 below:

TABLE 4

| First Aqueous Solution | | | Final Liposome Suspension | | |
|---|---|---|---|---|---|
| Leuprolide (mg/mL) | Sucrose (w/v %) | Other | Estimated Osmolarity (mOsm) | % Yield | Drug Loading (mg/mL) |
| 15 | 6.0 | 100 mM Phosphoric Acid | 328.6 | 56.2 | 10.9 |
| 15 | 4.0 | 100 mM Phosphoric Acid | 261.6 | 54.1 | 17.9 |

As in Examples 1 and 2 above, loading of leuprolide, a 9-amino acid peptide is modulated by varying the osmolarity of the first aqueous solution, with decreasing of osmolarity resulting in increased drug loading. A similar percent yield was maintained across the range of osmolarities tested. This result is also shown to be independent of the type of mixer used to generate the first and second emulsions in the manufacture of the MVLs.

EXAMPLE 4

Preparation of Morphine-containing Multivesicular Liposome Formulations

A lipid component containing DEPC, rather than DOPC, was prepared as in Example 1. The first aqueous component contained 17 mg/mL of morphine sulfate (Mallinckrodt Chemical Inc., St. Louis, Mo.) in 10 mM hydrochloric acid, and 0.2, 2.5 or 5.0 w/v % of sucrose as osmotic excipient. The remainder of the steps described in Example 1 were carried out to obtain MVLs containing morphine sulfate suspended in normal saline. The estimated osmolarity (mOsm), percent yield, and drug loading of these formulations are shown in Table 5 below:

TABLE 5

| First Aqueous Solution | | | Final Liposome Suspension | | |
|---|---|---|---|---|---|
| Morphine Sulfate (mg/mL) | Sucrose (w/v %) | Other | Estimated Osmolarity (mOsm) | % Yield | Drug Loading (mg/mL) |
| 17 | 4.8 | 10 mM HCl | 258.7 | 39.2 | 13.3 |
| 17 | 1.8 | 10 mM HCl | 162.7 | 58.5 | 23.1 |
| 17 | 0.2 | 10 mM HCl | 114.7 | 48.1 | 29.0 |

Again, loading of morphine, a lipid-soluble drug, was modulated by varying the osmolarity of the first aqueous solution, with decreasing of osmolarity resulting in increased drug loading. Percent yield of the MVL formulation was substantially equivalent across the osmolarity range tested.

EXAMPLE 5

Preparation of IGF-I-containing Multivesicular Liposome Formulations

1. A 0.5 mL Scale Preparation of MVLs.

A lipid component containing DEPC, rather than DOPC, was prepared as in Example 1. The first aqueous component contained 50 mg/ml, of IGF-I and 0.25, 0.5, 1.0, 2.5, or 5.0 w/v % of sucrose as osmotic excipient. The remainder of the steps described in Example 1 were carried out to obtain MVLs containing IGF-I suspended in normal saline. The estimated osmolarity (mOsm), percent yield, and drug loading of these formulations are shown in Table 6A below:

TABLE 6A

| First Aqueous Solution | | | Final Liposome Suspension | | |
|---|---|---|---|---|---|
| IGF-I (mg/mL) | Sucrose (w/v %) | Other | Estimated Osmolarity (mOsm) | % Yield | Drug Loading (mg/mL) |
| 20 | 5.0 | 100 mM HCl | 347.0 | 51.6 | 37.7 |
| 20 | 2.5 | 100 mM HCl | 267.0 | 47.5 | 46.1 |

TABLE 6A-continued

| First Aqueous Solution | | | Final Liposome Suspension | | |
|---|---|---|---|---|---|
| IGF-I (mg/mL) | Sucrose (w/v %) | Other | Estimated Osmolarity (mOsm) | % Yield | Drug Loading (mg/mL) |
| 50 | 2.5 | 100 mM HCl | 271.0 | 44.6 | 45.7 |
| 50 | 0.0 | 100 mM HCl | 195.0 | 53.4 | 73.2 |

Although loading of IGF-I was consistent with results obtained when citric acid was used as the buffer, then IGF-I showed some degradation in the studies conducted to characterize the encapsulated protein.

2. A 4 mL Scale Preparation of MVLs.

A lipid component containing DOPC, rather than DEPC, was prepared as in Example 1. A first set of formulations used a first aqueous component contained 20 mg/mL of IGF-I (Chiron Corp., Emeryville, Calif.) in 100 mM hydrochloric acid, and 2.5 or 5.0 w/v % of sucrose as osmotic excipient. A second set used 50 mg/mL of IGF-I in 100 mM hydrochloric acid and 0 or 2.5 w/v % of sucrose as osmotic excipient. The procedures of Example 1 were followed for obtaining the MVLs containing IGF-I, except that 4 mL of the first aqueous component was mixed with 4 mL of the lipid component using a TK Autohomogeneizer K at a speed of 9,000 rpm for 8 min to obtain the first emulsion. To the first emulsion, 16 mL of a solution containing 4 wt % glucose and 40 mM lysine (Spectrum Chemicals) was added, respectively. The resulting mixture was emulsified to form a second emulsion with the TK Autohomogeneizer K at a speed of 4,000 rpm for 1 min. The estimated osmolarity (mOsm), percent yield, and drug loading of these formulations using a vortexer mixer and DEPC, a lipid having a 22 carbon chain, shown in Table 6B below:

TABLE 6B

| First Aqueous Solution | | | Final Liposome Suspension | | |
|---|---|---|---|---|---|
| IGF-I (mg/mL) | Sucrose (w/v %) | Other | Estimated Osmolarity (mOsm) | % Yield | Drug Loading (mg/mL) |
| 50 | 5.0 | 0.0 | 162.7 | 57.0 | 49.8 |
| 50 | 2.5 | 0.0 | 82.7 | 62.4 | 76.8 |
| 50 | 1.0 | 0.0 | 36.7 | 54.9 | 97.4 |
| 50 | 0.5 | 0.0 | 21.7 | 66.0 | 157.1 |
| 50 | 0.25 | 0.0 | 14.2 | 67.0 | 159.4 |
| | 0 | | 6.7 | N/A | |

Table 6B shows that the loading obtained with the TK mixer procedure are similar to those obtained when a vortexer mixer is used to make the emulsions. However, the studies conducted to characterize the encapsulated protein showed increased presence of IGF-I oligomers in the absence of an acid buffer.

3. Preparation a 3 mL Scale MVL Formulation

A lipid component containing DEPC rather than DOPC was prepared as in Example 1. The first aqueous component contained one of the three formulations: (1) 30 mg/mL of IGF-I in 25 mM citric acid, and 0 or 2.5 w/v % of sucrose as osmotic excipient, (2) or 50 mg/mL of IGF-I in 25 mM citric acid, and 2.5, 1.0, 0.5 or 0 w/v % of sucrose, (3) or 50 mg/mL of IGF-I without citric acid, and 0 or 0.5 w/v % of sucrose. The procedures of Example 1 were followed for obtaining the MVLs containing IGF-I, except that 3 mL of the first aqueous component was mixed with 3 mL of the lipid component using an Omni Mixer ES at a speed of 10,000 rpm for 12 min to obtain the first emulsion. To the first emulsion, 20 mL of a solution containing 4 wt % glucose and 40 mM lysine (Spectrum Chemicals) was added, respectively. The resulting mixture was emulsified to form a second emulsion with the Omni Mixer ES at a speed of 4,500 rpm for 2 min. The estimated osmolarity (mOsm), percent yield, and drug loading of these formulations are shown in Table 6C below:

TABLE 6C

| First Aqueous Solution | | | | Final Liposome Suspension | |
|---|---|---|---|---|---|
| IGF-I (mg/mL) | Sucrose (w/v %) | Other | Estimated Osmolarity (mOsm) | % Yield | Drug Loading (mg/mL) |
| 30 | 2.5 | 25 mM Citric Acid | 106.8 | 69.2 | 54.8 |
| 30 | 0.0 | 25 mM Citric Acid | 30.8 | 57.2 | 132.2 |
| 50 | 0.5 | 0.0 | 21.7 | 80.0 | 171.4 |
| 50 | 0.0 | 0.0 | 6.7 | 72.7 | 267.5 |
| 50 | 2.5 | 25 mM Citric Acid | 109.5 | 60.3 | 82.5 |
| 50 | 1.0 | 25 mM Citric Acid | 63.5 | 72.3 | 138.2 |
| 50 | 0.5 | 25 mM Citric Acid | 48.5 | 71.5 | 174.2 |
| 50 | 0.0 | 25 mM Citric Acid | 33.5 | 65.8 | 175.7 |

The results in Table 6C show a similar modulation of drug loading by osmolarity for any of the drug concentrations tested.

EXAMPLE 6

A 125 ml Scale Preparation of Encapsulated IGF-I

A standard lipid component containing DEPC rather than DOPC was prepared as for other drug formulations. The first aqueous component contained 15 mg/mL IGF-I dissolved in either a 5% sucrose/20 mM ammonium citrate solution, or in a 8% sucrose/20 mM ammonium citrate solution. 125 mL of first aqueous solution was mixed with 125 mL of the lipid component using a high-shear double-mixing vessel system to obtain the first emulsion. This mixing system models the production scale process, and is used for scale-up of encapsulated drug formulations. The aqueous and organic components were mixed at a speed of 8000 rpm for 30 minutes in the first emulsion vessel. The first emulsion was then pumped at a rate of 167 mL/min into a fluid stream consisting of 0.04 N ammonium hydroxide in 1.5% glycine solution flowing at 2400 mL/min, and blended using an in-line static mixer to obtain the second emulsion. The total flow rate through the static mixer was 2567 mL/min. At this rate, the first emulsion was depleted in 90 seconds. The second emulsion, upon entry into a receiving vessel was mixed with lysine solution, and then was immediately sparged with nitrogen to strip off the organic solvent. The estimated osmolarity (mOsm), percent yield, drug loading, and % free-drug for these formulations are shown in Table 7 below.

TABLE 7

| First Aqueous Solution | | | | Final Liposome Suspension | | | | |
|---|---|---|---|---|---|---|---|---|
| IGF-I (mg/mL) | Sucrose (w/v %) | Other | Estimated Osmolarity | % Yield | Susp (mg/ml) | % Lipocrit | Drug Loading (mg/ml) | % Free IGF-I |
| 15 | 8.0 | 20 mM ammonium citrate | ~321 mOsm | 42 | 5.1 | 41.8 | 12.2 | 0.18 |
| 15 | 5.0 | 20 mM ammonium citrate | ~216 mOsm | 56 | 5.8 | 36.7 | 15.8 | 0.24 |

The results in Table 7 above show a similar increase in drug loading by decreased sucrose concentration as for the other drug formulations tested.

EXAMPLE 7

Effect of Substituting Glycylglycine as the Osmotic Excipient

A lipid component containing DEPC, rather than DOPC, was prepared as in Example 1. The first aqueous component contained 10 mg/mL of IGF-I in 25 mM citric acid, and 0, 1.0 or 2.0 w/v % of glycylglycine as osmotic excipient. The remainder of the steps described in Example 1 were carried out to obtain MVLs containing IGF-I suspended in normal saline. The estimated osmolarity (mOsm), percent yield, and drug loading of these formulations are shown in Table 6D below.

TABLE 6D

| First Aqueous Solution | | | | Final Liposome Suspension | |
|---|---|---|---|---|---|
| IGF-I (mg/mL) | Glycylglycine (w/v %) | Other | Estimated Osmolarity (mOsm) | % Yield | Drug Loading (mg/mL) |
| 10 | 2.0 | 25 mM Citric Acid | 180.1 | 64.0 | 10.4 |
| 10 | 1.0 | 25 mM Citric Acid | 104.1 | 53.0 | 13.0 |
| 10 | 0.0 | 25 mM Citric Acid | 28.1 | 41.7 | 24.4 |

A similar osmotic modulation of drug loading is shown for formulations using a non-sugar osmotic spacer, glycylglycine, in place of sucrose. Thus, the effect of osmolarity upon drug loading is shown by the data in Table 6D to be independent of the chemical structure of the osmotic excipient used.

Comparison of Different Osmotic Excipients at Equal Osmotic Strength

MVLs were made in the method of Example 1 containing IGF-I encapsulated with either 2.5 w/v % sucrose or 1.0 w/v % glycylglycine as osmotic excipients at approximately equal osmotic strength. For the comparison, 2.5 w/v % sucrose or 1.0 w/v % glycylglycine as the osmotic excipient was introduced into the first aqueous component containing 80 mg/mL IGF-I and 25 mM citric acid.

The procedures of Example 1 were followed for obtaining the MVLs containing IGF-I, except that 3 mL of the first aqueous component was mixed with 3 mL of the lipid component using an Omni Mixer ES at a speed of 10,000 rpm for 12 min to obtain the first emulsion. To the first emulsion, 20 mL of a solution containing 4 wt % glucose and 40 mM lysine (Spectrum Chemicals) was added, respectively. The resulting mixture was emulsified to form a second emulsion with the Omni Mixer ES at a speed of 4,500 rpm for 2 min.

To determine whether the effect upon drug loading is attributable solely to the osmolarity of the first aqueous component, a third formulation was made as described above, except that the concentrations of the osmotic excipient and the IGF-I were both proportionately decreased (from 80 mg/mL IGF-I and 2.5% sucrose to 50 mg/mL IGF-I and 1.0% sucrose. In this formulation, the second aqueous component substituted 1.5% glycine and 40 mM lysine in place of the 4% glucose and 40 mM lysine used in Example 1. Table 6E below compares the estimated osmolarity, % Yield and Drug Loading in the final liposome suspension for these three formulations.

A comparison of the estimated osmolarity (mOsm), percent yield, and drug loading of these formulations are shown in Table 6E below:

TABLE 6E

| First Aqueous Solution | | | Final Liposome Suspension | |
|---|---|---|---|---|
| IGF-I (mg/mL) | Osmotic Apacer (w/v %) | Other | Estimated Osmolarity (mOsm) | % Yield | Drug Loading (mg/mL) |
| 80(A) | 2.5% Sucrose | 25 mM Citric Acid | 113.5 | 85.9 | 145.1 |
| 80(B) | 1% Glycylglycine | 25 mM Citric Acid | 113.5 | 77.4 | 156.4 |
| 50(C) | 1% Sucrose | 25 mM Citric Acid | 63.5 | 75.7 | 142.5 |

The data in Table 6E show that the osmolarity of the osmotic excipient is the result effective variable because two different osmotic spacers at approximately equal osmotic strength, but at unequal molar concentration, produce a comparable effect upon drug loading.

EXAMPLE 8

Determination of Percent Encapsulation (or Percent Yield), Lipocrit, Percent Free Drug, Particle Size Distribution, and Drug Loading Tables 2 through 6A–E show the estimated osmolarity (mOsm), % Yield and Drug Loading (mg/mL) for the liposomal formulations described in Examples 1–6 above. These parameters were obtained as follows:

Percent encapsulation (or percent yield) of drug was calculated as the percent ratio of the amount of drug in the final liposome suspension to the total amount of drug used in the first aqueous solution. Thus, percent yield of drug was calculated as the ratio of the drug concentration in the final suspension times the volume of the final suspension to the drug concentration in the first aqueous solution times the volume of the first aqueous solution. Lipocrit was calculated, in analogy to hematocrit, as the percent ratio of the pellet volume to the suspension volume (see conditions below for obtaining the pellet volume).

Percent free drug was calculated as the percent ratio of the amount of drug in the supernatant to the amount of drug in the final suspension. Percent free drug can also be calculated as the percent ratio of the drug concentration in the supernatant to that in the suspension, times (1-lipocrit) Drug loading, which measures the amount of drug encapsulated in each unit of the encapsulated volume, is approximately equal to and can be estimated (assuming low percent free drug) as the ratio of the drug concentration of the final liposome suspension to the lipocrit. These variables were determined as more particularly described below.

To calculate the lipocrit about 50 $\mu$L of the multivesicular liposome suspension was taken up into a capillary tube, and end of the tube was sealed while ensuring that the suspension contained no air bubbles. The suspension was spun in a centrifuge at 600×g for 10 minutes to obtain a pellet layer and a supernatant layer. The percent ratio of the length of the tube occupied by the pellet to that occupied by the suspension gives the lipocrit.

For use in determining the amount of free drug in a formulation, supernatant was obtained by centrifuging about 0.2 mL of suspension for 3 min at 600×g in an Eppendorf centrifuge tube. For cytarabine and morphine formulations, 25–50 $\mu$L of the supernatant was withdrawn and pipetted into a glass tube containing 1 mL of 3:1 v/v isopropyl alcohol:1N hydrochloric acid (Fisher Chemical, Fair Lawn, N.J.), and rigorously mixed to obtain a clear solution. The absorbance at 280 nm for cytarabine, or at 285 nm for morphine was measured on a spectrophotometer (Hitachi U-2000). For leuprolide formulations, 50 $\mu$L of the supernatant was withdrawn and pipetted into a glass tube containing 2 mL of 1:1 isopropyl alcohol:water titrated to pH 10, using 0.1 N ammonium hydroxide, followed by rigorous mixing to obtain a clear solution.

The absorbance at 280 nm was then measured on a spectrophotometer (Hitachi U-2000). For enkephalin and IGF-I, 25–50 $\mu$L of the supernatant was withdrawn and pipetted into a glass tube containing 1 mL of 3:1 v/v isopropyl alcohol:2N citric acid (Sigma Chemical), followed by rigorous mixing to obtain a clear solution. The absorbance at 275 nm for enkephalin and IGF-I was measured on a spectrophotometer (Hitachi U-2000). Using a reference absorbance standard established based on drug solutions of known concentration in the same dissolving solution, the concentrations of drug in the suspension and supernatant were calculated.

Particle size distribution and particle mean diameter were determined by the method of laser light diffraction using a LA-500 or LA-910 Particle Size Analyzer from Horiba Inc. (Irvine, Calif.). The volume-weighted mean particle diameter for all the formulations studied was generally in the range from about 6 to 18 $\mu$m.

EXAMPLE 9

In Vitro and In vivo Release of High Drug Loading, High Percent Yield IGF-I Formulations The physicochemical integrity of the encapsulated IGF-I was confirmed by SDS-PAGE assay using Novex NuPage gel as well as by RP-HPLC assay using a C18 symmetric column. The encapsulated protein was extracted using 75:25 IPA:2N Citric Acid. The bioactivity of the encapsulated IGF-I was confirmed by a mitogenic bioassay using MG-63 human osteosarcoma cell line and 3-(4,5-dimethylthiazol-2-yl)-2,5-diphenyltetrazolium bromide (MTT) stain according to the method of W. Lopaczynski et al., *Regulatory Peptides*, 48:207–216, 1993. The MG-63 cells were obtained from the American Type Culture Collection (ATCC# CRL 1427), and the dose dependent mitogenic response of quiescent MG-63 cells to added IGF-I was determined. Bioactivity of extracted IGF-I was confirmed as approximately equivalent to that of an unencapsulated standard.

In Vitro Experiment: Briefly, an in vitro release experiment was set up and conducted as follows: a MVL suspension containing about 50 mg/mL of IGF-I was diluted 20-fold into human plasma containing 0.01% $NaN_3$; a 0.5 mL sample in screw-cap Eppendorf tube was used for each time-point, and samples were incubated under dynamic/rotating conditions at 37° C. Time-point samples were taken at various times and washed with 0.9 mL of normal saline. Particle pellets were then obtained by centrifugation in a microfuge at 16000 g for 4 minutes and stored at −20° C. until assayed by RP-HPLC using a C18 symmetric column. FIG. 1 shows some in vitro plasma release data obtained for the three representative IGF-I formulations listed in Table 6E. These data indicate that a sustained release of IGF-I is achieved over a period of longer than a week for high drug loading, high yield IGF-I formulations.

In vivo Experiment: Male rats were injected subcutaneously with the three MVL formulations shown in Table 6E to obtain information about in vivo release characteristics. Each rat received a 10 mg dose of IGF-I, and each of the formulations tested was injected into 3 rats. Blood samples (0.2 mL) were collected at time zero, and at 1, 3, 5 and 7 days post injection from the tail vein of the rats and allowed to clot. Serum was then obtained by centrifugation, and stored at −70° C. prior to assay for IGF-I concentration using an IGF-I ELISA kit DSL-10-5600 (Diagnostic Systems Laboratories Inc., Webster, Tex. according to the manufacturer's instructions.

Figure 2:
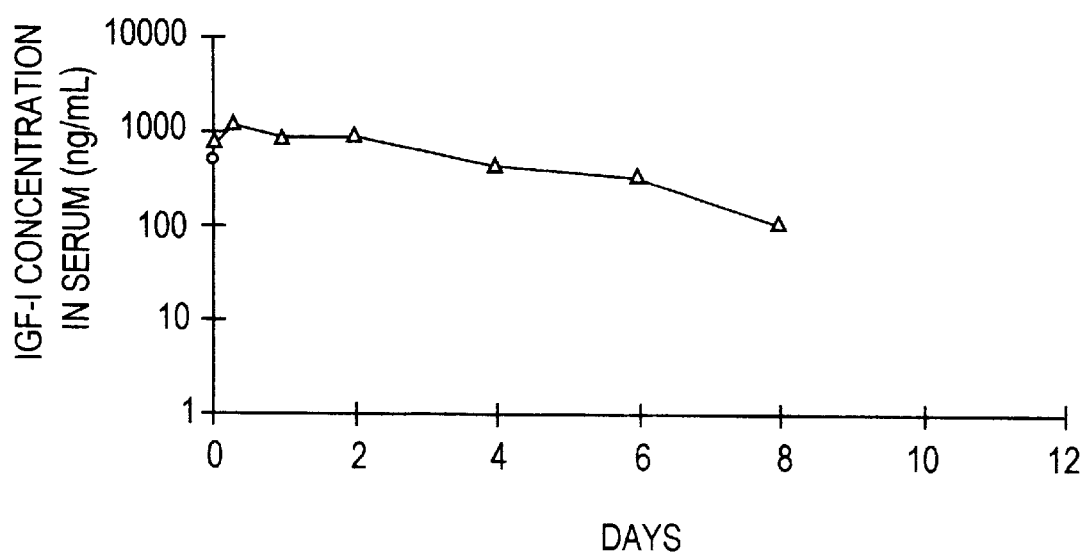
FIG. 2 is a graph showing the IGF-I concentration over 8 days in serum (mg/mL) of male rats after a 10 mg subcutaneous injection of MVLs containing 80 mg/mL IGF-I and 2.5 w/v % sucrose (113.5 mOsm) in the aqueous component. The data represent the mean of data for three rats.

FIG. 2 shows the time course of the average serum IGF-I concentration of three rats that received the 10 mg IGF-I of formulation A in Table 6E. These data indicate that a sustained serum level of IGF-I can be achieved over a period of many days using the high drug loading, high yield IGF-I formulations of this invention.

While presently preferred embodiments of the invention have been given for the purpose of disclosure, changes may be made therein which are within the spirit of the invention as defined by the scope of the appended claims.

What is claimed is:

1. A process for controlling loading of at least one biologically active agent into liposomes comprising:
   a) preparing a standard by dissolving at least one biologically active agent in an aqueous solution, wherein the resulting osmolarity of the aqueous solution is measured;
   b) forming liposomes by mixing the product of a) with a lipid component, thereby encapsulating said biological agent;
   c) measuring the amount of active agent encapsulated; and
   d) preparing modified liposomes by repeating steps a) and b) except that in a) the osmolarity is either further increased relative to the standard osmolarity, thereby decreasing loading of the agent; or further decreased relative to the standard osmolarity, thereby increasing loading of the agent.

2. The process of claim 1, wherein the modified aqueous solution further comprises an osmotic excipient in a concentration selected to modulate the osmolarity.

3. The process of claim 2, wherein the osmotic excipient is sucrose.

4. The process of claim 2, wherein the osmotic excipient is selected from the group consisting of glucose, glycine and glycylglycine.

5. The process of claim 1, wherein the modified osmolarity is in the range from about 0.01 mOsm to about 1100 mOsm.

6. The process of claim 1, wherein the modified osmolarity is in the range from about 5 mOsm to about 400 mOsm.

7. The process according to claim 1, wherein the biologically active agent is cytarabine.

8. The process according to claim 7, wherein the osmolarity of the modified aqueous solution is in the range from about 185 mOsm to about 450 mOsm.

9. The process according to claim 1, wherein the biologically active agent is morphine.

10. The process according to claim 9, wherein the modified osmolarity of the aqueous solution is in the range from about 114 mOsm to about 260 mOsm.

11. The process according to claim 1, wherein the biologically active agent is enkephalin.

12. The process according to claim 11, wherein the modified osmolarity of the aqueous solution is in the range from about 35.4 mOsm to about 191.5 mOsm.

13. The process according to claim 1, wherein the biologically active agent is leuprolide.

14. The process according to claim 13, wherein the modified osmolarity of the aqueous solution is in the range from about 261.6 mOsm to about 328.6 mOsm.

15. The process according to claim 2, wherein the osmotic excipient is selected from the group consisting of glycylglycine, glucose, sucrose, trehalose, succinate, cyclodextrin, arginine, galactose, mannose, maltose, mannitol, glycine, lysine, citrate, sorbitol, dextran, sodium chloride, and combinations thereof.

16. The process according to claim 1, wherein the biologically active agent is selected from the group consisting of an anesthetic, an antiasthmatic agent, a cardiac glycoside, an antihypertensive, a nucleic acid, an antibiotic, a vaccine, an anti-inflammatory, an antiarrhythmic, an antiangina, a hormone, an antidiabetic, an antineoplastic, an immunomodulator, an antifungal, a tranquilizer, a steroid, a sedative, an analgesic, a vasopressor an antiviral, a herbicide, a pesticide, a protein, a peptide, a neurotransmitter, a radionuclide, and suitable combinations thereof.

17. The process of claim 2, wherein the osmotic excipient is selected to decrease the osmolarity of the aqueous solution, whereby the loading of the biologically active agent is increased.

18. The process of claim 2, wherein the osmotic excipient is selected to increase the osmolarity of the aqueous solution, whereby the loading of the biologically active agent is decreased.

19. A process for controlling loading of at least one biologically active agent into multivesicular liposomes having multiple non-concentric chambers with membranes distributed as a continuous network throughout comprising the steps of:
   a) forming a standard first immiscible component by dissolving at least one biologically active agent in a first aqueous solution and then measuring the osmolarity;
   b) forming a second immiscible component by dissolving at least one amphipathic lipid and at least one neutral lipid in either one or more organic solvents, liquid $CO_2$, or liquid $NH_3$, thereby forming a lipid component;
   c) forming a water-in-oil emulsion by mixing the product of a) and b), thereby encapsulating said biologically active agent;
   d) dispersing the emulsion into a second aqueous component to form spherules;
   e) removing the organic solvent from the spherules to form multivesicular liposomes;
   f) measuring the amount of active agent encapsulated; and
   g) preparing modified liposomes by repeating steps a) through e), except that in a), the osmolarity of the first aqueous solution is either further increased relative to the standard osmolarity, thereby decreasing loading of the agent; or further decreased relative to the standard osmolarity, thereby increasing loading of the agent.

20. The process of claim 19, wherein the first aqueous component further comprises an osmotic excipient in a concentration selected to modulate the osmolarity.

21. The process of claim 20, wherein the osmotic excipient is sucrose.

22. The process of claim 20, wherein the osmotic excipient is selected from the group consisting of glucose, glycine, and glycylglycine.

23. The process of claim 19, wherein the modified osmolarity is in the range from about 0.01 mOsm to about 1100 mOsm.

24. The process of claim 19, wherein the modified osmolarity is in the range from about 5 mOsm to about 400 mOsm.

25. The process of claim 19, wherein the lipid component comprises at least one amphipathic lipid having from about 13 to about 28 carbons in its carbon chain.

26. The process of claim 19, wherein the lipid component comprises at least one amphipathic lipid having from about 18 about 22 carbons in its carbon chain.

27. The process of claim 19, wherein the amphipathic lipid comprises at least one zwitterionic amphipathic lipid.

28. The process of claim 19, wherein the amphipathic lipid comprises at least one cationic amphipathic lipid.

29. The process of claim 19, wherein the amphipathic lipid comprises at least one anionic amphipathic lipid.

30. The process according to claim 19, wherein the biologically active agent is cytarabine.

31. The process according to claim 30, wherein the modified osmolarity of the first aqueous component is in the range from about 185 mOsm to about 450 mOsm.

32. The process according to claim 19, wherein the biologically active agent is morphine.

33. The process according to claim 32, wherein the modified osmolarity of the first aqueous component is in the range from about 114 mOsm to about 200 mOsm.

34. The process according to claim 19, wherein the biologically active agent is enkephalin.

35. The process according to claim 34, wherein the modified osmolarity of the first aqueous component is in the range from about 35.4 mOsm to about 191.5 mOsm, and the corresponding loading of enkephalin is in the range from about 6.4 mg/mL to about 50.8 mg/mL of the formulation.

36. The process according to claim 19, wherein the biologically active agent is leuprolide.

37. The process according to claim 36, wherein the modified osmolarity of the first aqueous component is in the range from about 261.6 mOsm to about 328.6 mOsm.

38. The process according to claim 19, wherein the biologically active agent is IGF-I.

39. The process according to claim 38, wherein the first aqueous component further contains citric acid, the modified osmolarity of the first aqueous component is in the range from about 14.2 mOsm to about 347 mOsm, and the loading of IGF-I is in the range from about 10.4 mg/mL to about 175.7 mg/mL.

40. The process according to claim 19, wherein the second aqueous component comprises an osmotic excipient selected from the group consisting of glycylglycine, glucose, sucrose, trehalose, succinate, cyclodextrin, arginine, galactose, mannose, maltose, mannitol, glycine, lysine, glucuronic acid, citrate, sorbitol, dextran, sodium chloride, and combinations thereof.

41. The process according to claim 19, wherein the biologically active agent is selected from the group consisting of an anesthetic, an antiasthmatic agent, a cardiac glycoside, an antihypertensive, a nucleic acid, an antibiotic, a vaccine, an antiarrhythmics, an anti-inflammatory, an antiangina, a hormone, an antidiabetic, an antineoplastic, an immunomodulator, an antifungal, a tranquilizer, a steroid, a sedative, an analgesic, a vasopressor, an antiviral, a herbicide, a pesticide, a protein, a peptide, a neurotransmitter, a radionuclide, and suitable combinations thereof.

42. The process according to claim 19, wherein the osmolarity of the first aqueous component is chosen to modulate the rate of release of the biologically active agent from the multivesicular liposome into a physiologically relevant aqueous environment.

43. The process of claim 20, wherein the osmotic excipient is selected to decrease the osmolarity of the first aqueous component, whereby the loading of the biologically active agent is increased.

44. The process of claim 20, wherein the osmotic excipient is selected to increase the osmolarity of the first aqueous component, whereby the loading of the biologically active agent is decreased.

45. The process according to claim 19, wherein the neutral lipid is selected from the group consisting of triolein, tripalmitolein, tricaprin, trilinolein, trilourin, tricaprylin, squalene, and combinations thereof.

46. The process according to claim 19, wherein the organic solvent is selected from the group consisting of ethers, hydrocarbons, halogenated hydrocarbons, halogenated ethers, esters, $CHCl_3$, Freons, and combinations thereof.

* * * * *

UNITED STATES PATENT AND TRADEMARK OFFICE
CERTIFICATE OF CORRECTION

PATENT NO. : 6,106,858
DATED : August 22, 2000
INVENTOR(S) : Qiang Ye, Nandini Katre and Sankaram Bhima Mantripragada, Ph.D.

It is certified that error appears in the above-identified patent and that said Letters Patent is hereby corrected as shown below:

Title page,
Column 1, Last Reference, Ca[m]ncer Research
Column 2, First Reference, D[r]irect Cerebrospinal
Column 2, Last Reference, Narhi, et al.,
Following the Last Reference, please add the following references:

| | | |
|---|---|---|
| -- 4,078,052 | 03/07/78 | Papahadjopoulous |
| 4,089,801 | 05/16/78 | Schneider |
| 4,145,410 | 05/20/79 | Sears |
| 4,224,179 | 09/23/80 | Schneider |
| 4,235,871 | 11/25/80 | Papahadjopoulous, et al. |
| 4,310,506 | 01/12/82 | Baldeschwieler, et al. |
| 4,394,372 | 07/19/83 | Taylor |
| 4,522,803 | 06/11/85 | Lenk et al. |
| 4,588,578 | 05/13/86 | Fountain, et al. |
| 4,599,227 | 07/08/86 | Dees, et al. |
| 4,610,868 | 09/09/86 | Fountain, et al. |
| 4,752,425 | 06/21/88 | Martin, et al. |
| 4,769,250 | 09/06/88 | Forssen |
| 4,781,871 | 11/01/88 | West, III, et al. |
| 4,920,016 | 04/24/90 | Allen, et al. |
| 4,921,853 | May, 1990 | LeBlanc |
| 5,000,959 | 03/19/91 | Iga, et al. |
| 5,021,200 | 06/04/91 | Vanlerberghe, et al. -- |

FOREIGN PATENT OR PUBLISHED FOREIGN PATENT APPLICATION

GB 2050287   01/07/81   GB (UK) Application Pub.

OTHER DOCUMENTS

Huang, "Studies on Phosphatidylcholine Vesicles Formation and Physical Characteristics," *Biochemistry*, $\underline{8}$:334-352, 1969
Bangham, "Diffusion of Univalant Ions Across The Lamallae of Swollehn Phospholipids," *J. Mol. Bio.*, $\underline{13}$:238-252, *1965*
Szoka, et al., "Comparative Properties and Methods of Preparation of Lipid Vesicles (Liposomes), *Ann. Rev. Biophys. Bioengineering*, $\underline{9}$:467-508, 1980

UNITED STATES PATENT AND TRADEMARK OFFICE
CERTIFICATE OF CORRECTION

PATENT NO. : 6,106,858
DATED : August 22, 2000
INVENTOR(S) : Qiang Ye, Nandini Katre and Sankaram Bhima Mantripragada, Ph.D.

It is certified that error appears in the above-identified patent and that said Letters Patent is hereby corrected as shown below:

Column 2,
Line 11, process to control the rate of release in biological fluids [(] of Column 6,
Line 10, phosphatidylethanolamines, sphingomyelins, etc. Examples Column 7,
Line 56, Volume of Liposome Suspension)

Column 10,
Line 50, cines, etc. Of particular interest are interleukin-2, insulin-like Column 16,
Line 57, 3. Preparation of a 3mL Scale MVL Formulation Column 19,
Line 48, liposomal formulations described in Examples 1-[6]7 above.

Column 24,
Line 19, antiangial, a hormone, an antidiabetic, an antineoplastic, an Signed and Sealed this Eighth Day of January, 2002

*Attest:*

JAMES E. ROGAN
*Attesting Officer*    Director of the United States Patent and Trademark Office